United States Patent
Dardelle et al.

(10) Patent No.: US 10,034,819 B2
(45) Date of Patent: Jul. 31, 2018

(54) MULTILAYERED CORE/SHELL MICROCAPSULES

(71) Applicant: FIRMENICH SA, Geneva (CH)

(72) Inventors: Grégory Dardelle, Geneva (CH); Marlène Jacquemond, Geneva (CH); Philipp Erni, Geneva (CH)

(73) Assignee: Firmenich SA, Geneva (CH)

( * ) Notice: Subject to any disclaimer, the term of this patent is extended or adjusted under 35 U.S.C. 154(b) by 99 days.

(21) Appl. No.: 14/431,275

(22) PCT Filed: Sep. 23, 2013

(86) PCT No.: PCT/EP2013/069681
§ 371 (c)(1),
(2) Date: Apr. 7, 2015

(87) PCT Pub. No.: WO2014/044840
PCT Pub. Date: Mar. 27, 2014

(65) Prior Publication Data
US 2015/0250689 A1    Sep. 10, 2015

(30) Foreign Application Priority Data
Sep. 24, 2012   (EP) .................................... 12185741

(51) Int. Cl.
C11D 3/50 (2006.01)
C11D 17/00 (2006.01)
(Continued)

(52) U.S. Cl.
CPC .................. *A61K 8/11* (2013.01); *A61K 8/65* (2013.01); *A61K 8/73* (2013.01); *A61K 8/84* (2013.01);
(Continued)

(58) Field of Classification Search
None
See application file for complete search history.

(56) References Cited

U.S. PATENT DOCUMENTS

| 4,137,180 A | 1/1979 | Naik et al. |
| 4,891,172 A * | 1/1990 | Matsushita ............. B01J 13/18 264/4.3 |

(Continued)

FOREIGN PATENT DOCUMENTS

| DE | 3030801 A1 | 4/1981 |
| EP | 799885 A1 | 10/1997 |

(Continued)

OTHER PUBLICATIONS

Meyer, "Perfume Microencapsulation by Complex Coacervation," Chimia, 46:101-102 (1992).
(Continued)

*Primary Examiner* — Lorna M Douyon
(74) *Attorney, Agent, or Firm* — Winston & Strawn LLP (57) ABSTRACT

The invention relates to a method of making multilayer core/shell microcapsules for delivery of active agents such as fragrance components of perfume oils. The method includes forming an outer shell by coacervation surrounding an internal phase which contains the active agent; and forming an inner shell by interfacial polymerization at the interface between the internal phase and the outer shell. The internal phase contains the active agent. The microcapsules are typically incorporated in a consumer product wherein the multilayer shell prevents the active agent from release until desired, generally during use of the consumer product.

14 Claims, 7 Drawing Sheets

(51) Int. Cl.

| | | |
|---|---|---|
| A61K 8/11 | (2006.01) | |
| A61K 8/73 | (2006.01) | |
| A61K 8/84 | (2006.01) | |
| B01J 13/16 | (2006.01) | |
| B01J 13/14 | (2006.01) | |
| B01J 13/10 | (2006.01) | |
| B01J 13/22 | (2006.01) | |
| C11B 9/00 | (2006.01) | |
| A61Q 15/00 | (2006.01) | |
| A61K 8/65 | (2006.01) | |
| A61K 8/87 | (2006.01) | |
| A61Q 19/10 | (2006.01) | |
| A61Q 5/02 | (2006.01) | |
| A61Q 5/12 | (2006.01) | |

(52) U.S. Cl.
CPC ............ *A61K 8/87* (2013.01); *A61Q 15/00* (2013.01); *B01J 13/10* (2013.01); *B01J 13/14* (2013.01); *B01J 13/16* (2013.01); *B01J 13/22* (2013.01); *C11B 9/00* (2013.01); *C11D 3/505* (2013.01); *A61K 2800/412* (2013.01); *A61Q 5/02* (2013.01); *A61Q 5/12* (2013.01); *A61Q 19/10* (2013.01)

(56) References Cited

U.S. PATENT DOCUMENTS

| | | |
|---|---|---|
| 5,180,637 A | 1/1993 | Sumii |
| 5,236,615 A | 8/1993 | Trinh et al. |
| 5,635,211 A * | 6/1997 | Nehen ................ A01N 25/28 264/4.1 |
| 2005/0067726 A1 * | 3/2005 | Yan ..................... A23L 33/12 264/4.1 |
| 2005/0112152 A1 | 5/2005 | Popplewell et al. |
| 2005/0276831 A1 * | 12/2005 | Dihora .................. A61K 8/11 424/401 |
| 2010/0323945 A1 * | 12/2010 | Simonsen ............. C11D 3/222 510/360 |

FOREIGN PATENT DOCUMENTS

| | | | |
|---|---|---|---|
| EP | 1533364 A2 | | 5/2005 |
| GB | 1141186 | * | 1/1969 |
| GB | 1141186 A | | 1/1969 |
| GB | 1 257 178 A | | 12/1971 |
| GB | 1257178 | * | 12/1971 |
| WO | 97/34986 A1 | | 9/1997 |
| WO | WO1997034986 A1 | | 9/1997 |

OTHER PUBLICATIONS

International Search Report and Written Opinion, application PCT/EP2013/069681, dated Nov. 6, 2013.
Erni et al., Angew, Chem Int. Ed. 2013, 52, p. 10334-10338.
Erni et al., Review of Scientific Instruments, vol. 74, pp. 4916-4924, 2003.
Fan et al., Materials Science Forum, 2011, vol. 675-677 (Advanced Material Science and Technology) p. 1109-1112.
Parker A. et al., Soft Matter 2010, 6, pp. 4916-4919.
Ullman's Encyclopedia of Industrial Chemistry, vol. A8, 1987, p. 315-448.
Ullman's Encyclopedia of Industrial Chemistry. vol. A25, 1994, p. 747-817.

* cited by examiner

MULTILAYERED CORE/SHELL MICROCAPSULES

FIELD OF THE INVENTION

The invention relates to a delivery system comprising both a core and a multilayered, composite shell formed by a coacervate and synthetic polymer, and the use of the delivery system for encapsulating a liquid, a solid, an emulsion or a dispersion containing a fragrance or flavor component.

BACKGROUND OF THE INVENTION

Perfume additives make consumer products such as home and body care products, and in particular laundry compositions, more aesthetically pleasing to the consumer and in many cases the perfume imparts a pleasant fragrance to fabrics treated therewith. The amount of perfume carryover from an aqueous laundry bath onto fabrics, however, is often marginal. By encapsulating perfume additives in microcapsules, the delivery efficiency and active lifetime of the perfume additives can be improved. Microcapsules provide several advantages, such as protecting the perfume from physical or chemical reactions with incompatible ingredients in the laundry composition, as well as protecting the perfume from volatilization or evaporation. Microcapsules can be particularly effective in the delivery and preservation of perfumes in that the perfumes can be delivered to and retained within the fabric by a microcapsule that only ruptures, and therefore releases the perfume, when the fabric is dry. The rupture of microcapsules can be induced by various factors such as temperature so that the contents are delivered when the capsule degrades. Alternatively the microcapsules can be compromised by physical forces, such as crushing, or other methods that compromise the integrity of the microcapsules. Additionally, the microcapsule contents may be delivered via diffusion through the capsule wall during a desired time interval.

Scent associated with laundered laundry is important to many consumers. There are many so called "touch points" that consumers associated with during the laundry experience. Non-limiting examples of these touch points include the freshness experience associated with opening a fabric care container, opening a washing machine after washing laundry, opening a laundry dryer after drying laundry, and freshness associated with wearing laundered clothes. It has been reported that there is a significant portion of consumers that will fold and put away their laundry about one day after having laundered laundry. Freshness while folding laundry about one day after having laundered laundry also signals to the consumer that the laundry is clean.

Multilayered capsules are known in the art. US 2005/0112152 generally describes encapsulated fragrance further coated with a second coating, such as a cationic coating. British patent application GB 1257178 discloses multi-coated capsules produced by forming a secondary film layer at the interfaces of hydrophilic and hydrophobic liquids in the defective parts of the already formed primary film layer, e.g., crackles, capillary micropores or the like present therein, to fill up the defects.

British patent application GB 1141186 discloses dual walled capsules produced by first precoating droplets or solid particles of an internal phase in an aqueous vehicle through an interfacial reaction between two reactants, one of which is present in the aqueous vehicle, the other being present in or on the internal phase; and then providing another coating by coacervation.

U.S. Pat. No. 5,180,637 describes double-walled microcapsules wherein the primary wall is composed of an amino resin prepared by polycondensation reaction and the secondary wall is formed by coacervation of a polyion complex of the resin with polystyrenesulfonic acid or salt thereof, whereby liquid droplets are deposited on the primary wall. While those microcapsules are said to have improved resistance to heat and moisture, the structure of the shell consisting of superposed distinct layers is likely to delaminate and provide products which are still highly permeable.

Fan et al. reports preparing microcapsules with triallylamine-containing core surrounded by polyelectrolyte shell of controlled thickness via layer-by-layer assembly technology ("Preparation of oil core/multilayerpolyelectrolyte shell microcapsules by a coacervation method," Materials Science Forum (2011), vol. 675-677 (Pt. 2, Adv. Mat. Science and Technology), p. 1109-1112).

Although multilayered capsules are generally known in the art, the quality of these capsules is far from satisfactory. Thus, there is a need in the industry for microcapsules with improved barrier and release properties for encapsulated materials such as perfumes. The present invention satisfies this and other needs of the industry.

SUMMARY OF THE INVENTION

The invention relates to a method of making multilayered microcapsules which comprises providing as a dispersion in an aqueous vehicle, a hydrophobic internal phase comprising a monomer and an active agent of a fragrancing or flavouring component such as a perfume or flavor oil; mixing a first and second polyelectrolytes in the aqueous vehicle under conditions sufficient to form a suspension of complex coacervate nodules; depositing the complex coacervate nodules at an interface of an aqueous vehicle adjacent the hydrophobic internal phase to form an outer shell of the microcapsule, wherein the hydrophobic internal phase forms the core and contains the monomer and fragrancing or flavouring component therein; and introducing a water soluble reactant into the aqueous vehicle under conditions sufficient to induce interfacial polymerization of the monomer inside the outer shell to form an inner shell at the interface between the internal phase and the outer shell.

Advantageously, the outer shell provides a scaffold upon which the monomer is polymerized, and the inner shell is formed as a layer that is interlinked with the outer shell, instead of providing distinct independent layers obtained with processes like those described heretofore. Also, the first polyelectrolyte may be positively charged when the pH is less than 8 while the second polyelectrolyte may be negatively charged when the pH is greater than 2 such that the outer shell comprises a hydrogel. The first polyelectrolyte is preferably gelatin while the second polyelectrolyte is preferably acacia gum. The monomer is preferably an oil soluble isocyanate, and the reactant is preferably guanazol, guanidine, or a salt thereof.

The method optionally further comprises cross-linking the core-shell capsule chemically or enzymatically before introducing the reactant into the aqueous vehicle. Also, the pH and temperature of the aqueous vehicle can be adjusted before, during, or after the introduction of reactant to control the rate of interfacial polymerization. The reaction is generally conducted to provide the inner shell with a volume that is between 10 and 25% and preferably 12 to 20% of the volume of the outer shell. Also, the microcapsules generally have a size of between 5 µm to 1,000 µm.

The invention also relates to a multilayered microcapsule produced by the methods disclosed herein. These multilayer microcapsules generally comprise an outer shell of a coacervate, an inner shell of a synthetic polymer, preferably polyurea, and an internal phase comprising an active agent of a fragrancing or flavouring component such as a perfume or flavor oil wherein, advantageously, the outer coacervate shell and the inner polymer shell form a composite, interlinked structure that does not delaminate. This novel composite structure is at the origin of the improved barrier properties of the capsules.

The invention also relates to the use of the multilayered microcapsules disclosed herein as a perfuming composition for consumer products. These consumer products are generally in the form of a home- or personal-care product that includes the multilayered microcapsules therein, and are preferably in liquid or powder form specifically as a detergent composition, a fabric softener, a hard surface cleaning composition, or a dishwashing composition, or a shampoo, a hair conditioner, a shower or bath mousse, oil or gel, a deodorant, or an antiperspirant.

BRIEF DESCRIPTION OF THE DRAWINGS

FIGS. 3A and B show standard coacervate capsules (A) and the multilayered (coacervate/polyurea) core/shell capsules (B) in a shower gel after 24 hrs.

DETAILED DESCRIPTION OF THE INVENTION

The present invention provides core-shell microcapsules having dual wall shells of a coacervate and synthetic polymer composite structure, and preferably of a hydrogel/polyurea composite structure. Such membrane compositions and particular structure have been designed and have shown to provide benefits such as improved bather properties for encapsulated material; improved adhesive properties; adjustable release properties; desired mechanical properties; tuned shell density of the capsule; and, optionally, improved processability and facilitated drying of the capsules.

Figure 1:
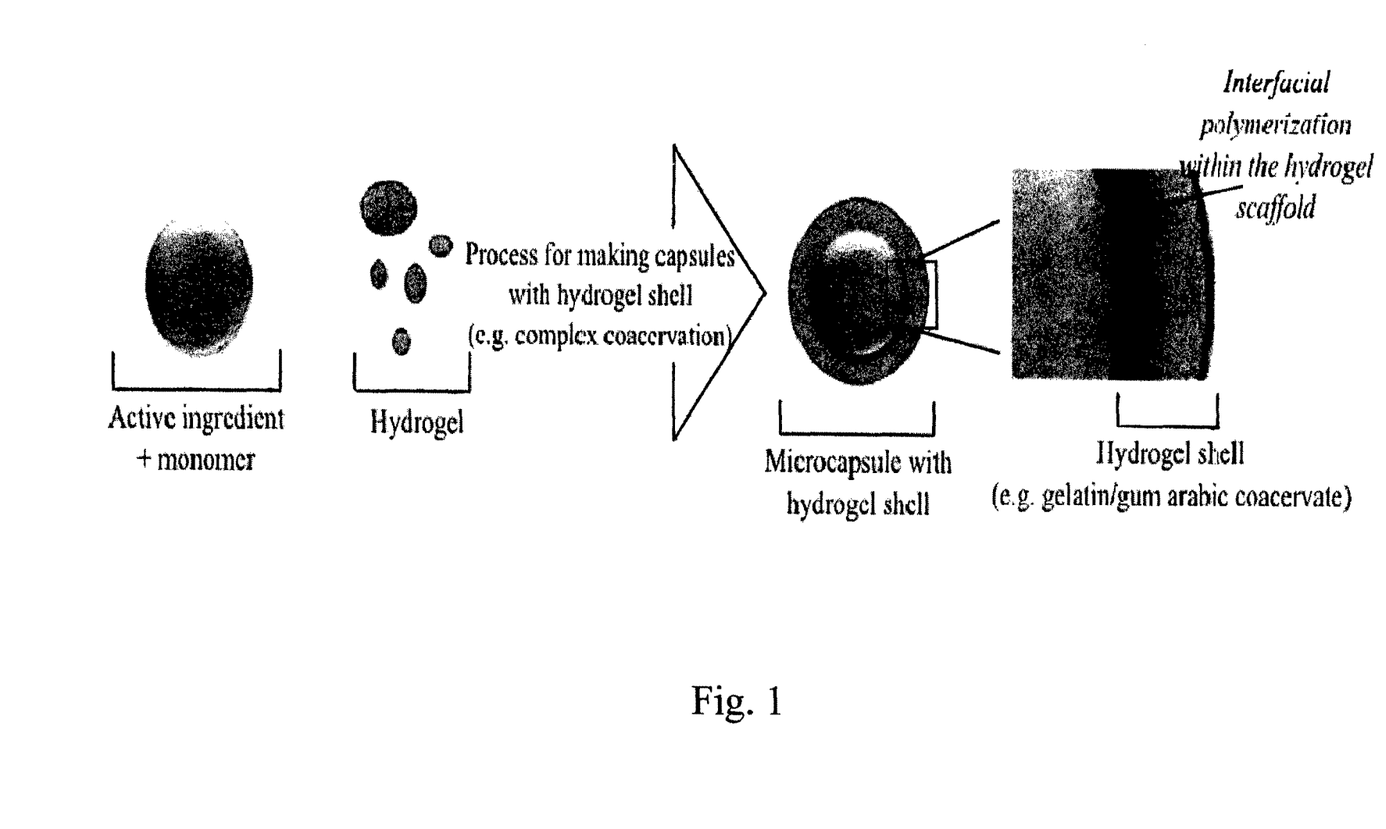
FIG. 1 is a diagram showing a process for making the multilayered core/shell capsules of the invention.
Figure 4:
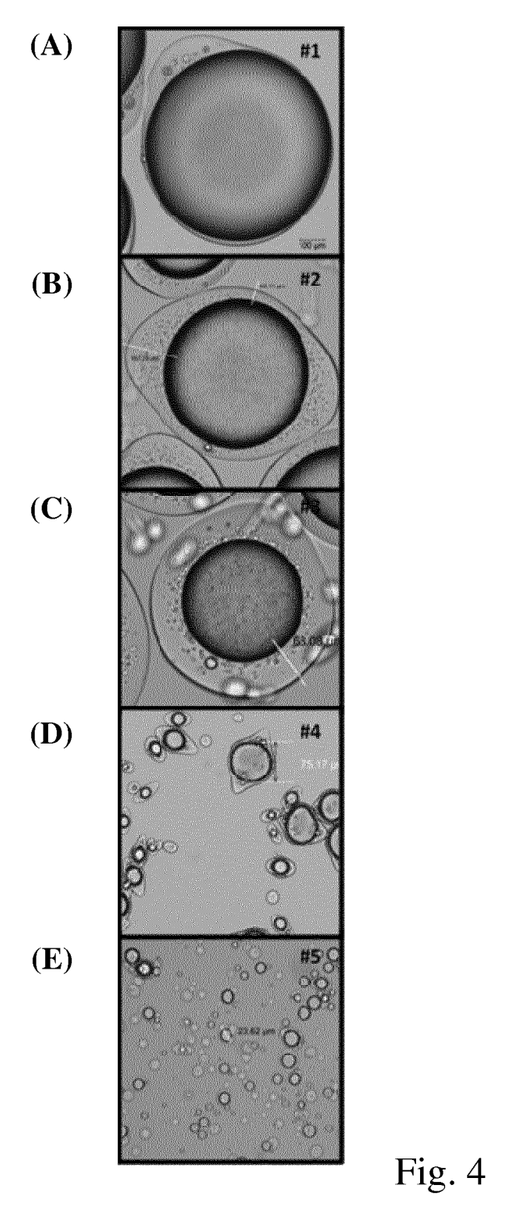
FIGS. 4A-E show exemplary capsules of the invention having different sizes and membrane thickness.

The general concept of the invention is to combine two processes, namely, the complex coacervation process (for the outer hydrogel shell) and an interfacial polymerization process (for the inner polymer shell) in a particular order to obtain core/multilayer shell capsules having improved properties. The coacervate constituting the outer shell of the capsule acts as a scaffold for the polymerization of the inner polymer shell. Such combination results in the formation of a composite membrane with two interlinked layers. By composite membrane with two interlinked layers, it is meant a membrane consisting of layers that are linked by chemical bonds, thereby forming one inseperable entity. The structure is therefore such that the outer coacervate is covalently linked to the inner polymer shell (shown schematically in FIG. 1, and in the micrographs on FIG. 4). Surprisingly, such composite membranes with interlinked layers remain interlinked even upon mechanical breakage, therefore they undergo breakage as a whole (rather than delaminating or breaking one layer after the other). Without being bound by theory it is believed that the monomer present in the internal phase is reacting with the amine functionalities of the electrolyte (e.g. amine functionality of protein) even before the water soluble reactant is added to induce interfacial polymerization. Using mechanical measurements on the membrane material, described below in the Examples, it was found here that if multilayered capsules are prepared following the invention, the polyelectrolyte participates in the interfacial polymerization, thereby getting intimately integrated into the membrane. Also, by conducting both the complex coacervation and interfacial polymerization processes within the same process unit, the method of the present invention advantageously reduces the process time and cost while also providing capsules that exhibit the improved properties defined herein.

Figure 5:
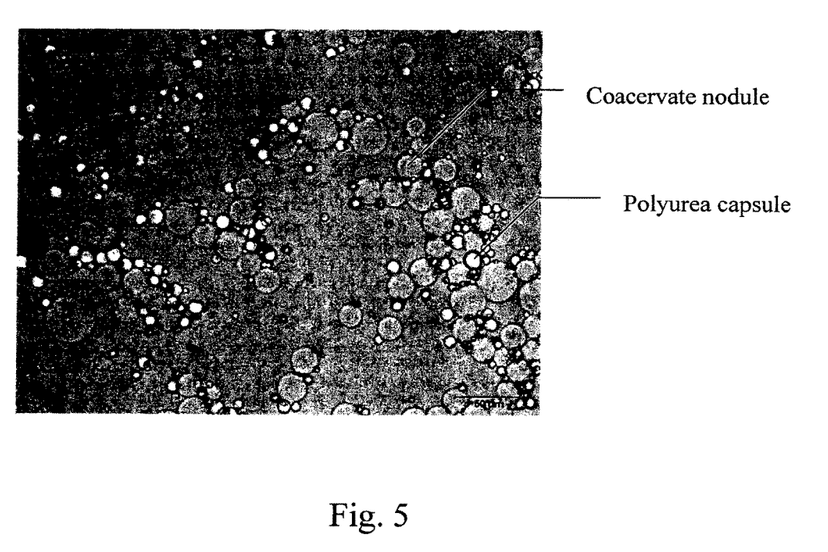
FIG. 5 shows a comparative experiment wherein coacervate nodules did not deposit at the microcapsule surface and instead remain dispersed.

Although the complex coacervation process and the interfacial polymerization process are each known in the art, it is believed that these processes have not previously been combined successfully due to technical difficulties. It is not possible to simply associate these two different processes to build microcapsules with two (or more) distinct walls. One possible way may be for the skilled person to start by creating a standard aqueous suspension of synthetic microcapsules made by interfacial polymerization and then deposit on the surface of the primary microcapsule, a hydrogel following the process of complex coacervation. This type of approach is disclosed in British patent application GB 1141186 but is unsuitable because the polymer phase separation (i.e., complex coacervation) occurs in a range of pH which is "non-conventional" for the polymerization process. Therefore, the simple addition of the state of the art of two processes one after the other will not work. In fact, comparative experiments were performed following the approach disclosed in GB 1141186. The objective was to form a membrane of coacervate onto polyurea microcapsules. This process proved unsuccessful, as the coacervate nodules did not deposit at the microcapsule surface and stayed in the continuous aqueous media, and this is shown in FIG. 5 wherein the two separate populations of particles (coacervate nodule and polyurea microcapsules) can be seen.

In contrast, the present invention induces a specific modification of the membrane of the primary microcapsule that is initially made by complex coacervation in order to obtain coacervated microcapsules exhibiting high barrier properties (i.e., low permeability). Typically, the specific membrane modification is carried out by inducing polymerization within the coacervate, which is typically a hydrogel. This local reinforcement is only permitted if the polymerization starts from inside of the microcapsule, so that the primary microcapsule is provided with a monomer within its core. This is achieved by adding a monomer that is unreactive with the other components that are present in the coacervation process, and then by polymerizing the monomer in the capsules after the capsules are formed. The compatibility of the two processes is not an issue as in the prior art.

A typical process for making the microcapsule of the present invention comprises the following steps:

I. Formation of the First, Outer Hydrogel Shell by Complex Coacervation

Two oppositely charged polyelectrolytes are mixed under specific temperature, pH and concentration conditions to induce polymer phase separation, so as to produce a suspension of complex coacervate nodules. The complex coacervate nodules have to deposit at the active interface to form core-shell capsules. Optionally, the capsules undergo a chemical or enzymatic cross-linking step. Furthermore, the active agent to be encapsulated, typically a fragrancing material such as a perfume oil, must already contain the appropriate monomer (e.g., an isocyanate) which is later polymerized to form the inner shell.

II. Formation of the Second, Inner Shell by Polymerization at the Coacervate/Oil Interface The polymerization of the monomer contained within the core of the capsule is induced by introducing a water soluble reactant in the continuous phase. The coacervate or hydrogel shell is needed to provide a scaffold upon which the synthetic polymer may be polymerized. The reactant is dependent of the nature of the monomer. In a preferred embodiment the polymerization reaction is induced between an isocyanate and an amine (or diamine) to obtain a polyurea polymer. This is generally achieved by first adjusting the pH and then introducing, preferably drop wise or in portions, a solution of an amine (or diamine) into the capsule dispersion. The polymerization is then induced at the hydrogel/oil interface, thereby forming the second, inner, polyurea shell. The monomer contained within the core of the capsule and the reactant introduced in the aqueous continuous phase wherein the capsules are dispersed, are both needed to induce the polymerization and finally the formation of the inner shell (e.g., polyurea). Preferably, the reactant is introduced slowly. Typically, the pH and the temperature of the capsule suspension are tuned, before, during, or after the introduction of reactant, to control the polymerization time.

In the microcapsules of the invention, the hydrogel shell (coacervate) improves the adhesion and the mechanical properties of the capsule while the inner shell (polyurea) provides additional and superior barrier properties to obtain a microcapsules that exhibits excellent resistance against evaporation of the active agent when the capsules are in the dry state as well as excellent resistance against destabilization of the capsules in harsh environments, e.g., in detergent or surfactant solutions.

Typically, the microcapsules of the invention are made from the following preferred ingredients:
(1) A first polyelectrolyte (Polyelectrolyte I) of one charge, preferably selected among proteins that are able to interact with an electrolyte or polyelectrolyte that has an opposite charge to thus form a coacervate phase having the ability to coat hydrophobic interfaces in order to form the capsules. In a preferred embodiment, Polyelectrolyte I is positively charged for pH<8 so as to form gels or highly viscous solutions in water below the gelling temperature, and lower viscosity solutions in water at a temperature above the melting point of the gel. The viscosity above the gelling temperature is typically lower than 0.1 Pa·s; below the gelling temperature, the elastic modulus G' of the gel is typically in the range 0.1-15 kPa when measured during the first 24 hours after gel formation, using the measurement methods based on shear rheometry (such methods, along with the definitions relevant for the gelling temperature, are described, for example, in Parker, A. and Normand, V., *Soft Matter*, 6, pp 4916-4919 (2010). During the coacervation process, the temperature of oil introduction may be adjusted to a value sufficient to shorten the membrane formation step and avoid premature reaction of the isocyanate at the oil/water interface. Preferably, Polyelectrolyte I is a gelatin material.
(2) A second polyelectrolyte (Polyelectrolyte II), which is preferably selected among polysaccharides or another polymer bearing charges of opposite polarity compared to Polyelectrolyte I. Generally, Polyelectrolyte II is negatively charged for pH>2. Preferably, Polyelectrolyte II is a polyelectrolyte that is only weakly negatively charged at pH>2; such polyelectrolytes are, for example, carboxymethyl cellulose, sodium carboxymethyl guar gum, or xanthan gum, or yet plant gums such as acacia gum. Most preferably, it is acacia gum (gum arabic). The ratio between polyelectrolyte 1 and polyelectrolyte 2 is preferably comprised between 10/0.1 to 0.1/10.
(3) A monomer which is typically soluble in oil and able to interact and polymerize with a water soluble reactant. Preferably, the monomer is an isocyanate.
(4) A reactant for the monomer, which reactant is soluble in water and is generally selected from water soluble compounds selected from the group consisting of diamines, polyols, alcohols and other reactants that are able to induce the polymerization of the monomer that is contained in the core of the capsule. Preferred reactants include guanazol or guanidine.
(5) An active agent which is encapsulated within the microcapsules. By "active agent" what is meant is a volatile material that would be rapidly released. Any type of volatile material can be used, including flavors and fragrances, but the present microcapsules are ideally suitable for encapsulating fragrancing components such as perfume oils.

The terms "flavors" and "fragrances" as used herein are deemed to define a variety of flavour and fragrance materials of both natural and synthetic origin. They include single compounds or mixtures. Specific examples of such components may be found in the literature, e.g. in Fenarsoli's handbook of Flavor Ingredients, 1975, CRC Press; synthetic Food Adjuncts, 1947 by M. B. Jacobs, edited by van Nostrand; or Perfume and Flavor Chemicals by S. Arctander 1969, Montclair, N.J. (USA), or any more recent versions of such textbooks. These substances are well known to the person skilled in the art of perfuming, flavoring and/or aromatising consumer products, i.e. of imparting an odour and/or flavour or taste to a consumer product traditionally perfumed or flavoured, or of modifying the odour and/or taste of the consumer product.

Accordingly, in an embodiment, the ingredient comprises at least 5 wt. %, preferably at least 10 wt. %, preferably at least 20 wt. %, more preferably at least 30 wt. % and most preferably at least 40 wt. % of chemical compounds having a vapour pressure of ≥0.007 Pa at 25° C.

Preferably, at least 10 wt. % have a vapour pressure of ≥0.1, more preferably, at least 10 wt. % have a vapour pressure of ≥1 Pa at 25° C., and most preferably, at least 10 wt. % have a vapour pressure of ≥10 Pa at 25° C. The value of 0.007 Pa at 25° C. is selected because it encompasses most of the compounds used by the skilled flavourist and/or perfumer. Compounds meeting these criteria are generally regarded as having a volatile character. In addition, compounds that remain odourless due to a lower volatility are excluded. The limit of 1 wt. % of such compounds is regarded to constitute a substantial part of the ingredient. The method of the present invention, however, allows for efficient encapsulation of more volatile ingredients being present in higher amounts of the total ingredients.

For the purpose of the present invention and for the sake of convenience, the vapour pressure is determined by calculation. Accordingly, the method disclosed in "EPI suite"; 2000 U.S. Environmental Protection Agency, is used to determine the concrete value of the vapour pressure of a specific compound or component of the ingredient. This software is freely available and is based on average values of vapour pressures obtained by various methods of different scientists.

The fragrance compound limonene is adduced for illustrating the determination of vapour pressure by calculation: by applying the method "EPI suite", limonene is calculated to have a vapour pressure of about 193 Pa at 25° C.

The monomer that is used in the process of the invention preferably has at least two isocyanate groups, and more preferably, at least three isocyanate groups. With these functional groups, an optimal reticulation or network of the capsule wall is achieved, providing thus microcapsules exhibiting a surprisingly useful dual shell barrier that provides a prolonged slow release of fragrance, as well as a surprisingly improved stability of the microcapsules in a wide range of consumer products. Low volatility aliphatic polyisocyanate products are especially preferred because of their low toxicity. Such products are characterized by a low concentration of monomeric hexamethylene diisocanate (HDI); typically, such products contain at most 0.7% HDI and are available commercially. In particular, the isocyanate monomer is preferably hexamethylene diisocyanate or isophorone diisocyanate.

In the process of the invention, the reactant is preferably selected from the group of water soluble guanidine salts and guanidine. By "water soluble guanidine salt," it is meant a salt soluble in water and resulting from the reaction of guanidine with an acid. One example of such salts is guanidine carbonate. The polyurea wall of the microcapsules is the result of the interfacial polymerization between the monomer in the internal phase and the reactant. Preferably, for each mole of isocyanate monomer contained in the internal phase, 1 to 3 moles, and preferably 1.2 to 2 moles, of guanidine or guanidine salt are added for the interfacial polymerization. Accordingly, an excess of the reactant is provided to assure complete polymerization of the monomer. No specific action is required to induce the polymerization between the isocyanate monomer and the guanidine or guanidine salt in the dispersion. The reaction starts immediately after adding the reactant. Preferably, the reactant is added slowly with the reaction maintained for 2 to 15 hours, and preferably for 4 to 10 hours. The specific composition of the polyurea wall is key in obtaining dual wall microcapsules that include a fine balance between release and retention so as to achieve satisfactory slow and constant release of the encapsulated fragrance component over time, such as when the capsules are eventually placed on textiles or hair, while also exhibiting the desired stability in the product base (e.g., counteracting efficiently the extraction of the perfume by the surfactants contained in the consumer product). The combination of isocyanate and guanidine or guanidine salts enable this fine tuning of the properties and stability of the capsules. Of course, skilled artisans can select other combinations of monomers and reactants to achieve the desired results for any particular microcapsules for fragrancing of a specific consumer product.

The multilayered microcapsule of the present invention is a core/multilayershell system comprising a membrane which typically contains gelatin, gum arabic and water; and an internal phase which typically contains a monomer (e.g., the isocyanate) and the active agent (e.g., a fragrancing component such as a perfume oil). The relative proportion of each constituent within the microcapsule of the invention varies, depending on the mean diameter and the thickness of the membrane that is to be formed. Table I below shows exemplary microcapsules of the invention having different sizes and membrane thickness. The morphologies of five types of microcapsules (Samples #1 to #5) are shown in FIGS. 4A-E. The volume fraction of the membrane represents less than 15% for a "large" microcapsule having a thin membrane (e.g., Sample #1, FIG. 4A) and reaches up to 80% for a "small" capsule having a thick membrane (e.g., Sample #5, FIG. 4E).

TABLE I

Multilayered Microcapsules having different sizes and membrane thickness. Numbers # refer to image in FIG. 4

| | # | Core radius (μm) | Outer shell thickness (μm) | Volume fraction inner shell:total shell Type 1 (polyurea thin) % v/v | Volume fraction inner shell:total shell Type 2 (polyurea thick) % v/v |
|---|---|---|---|---|---|
| Thick outer shell | 5 | 10 | 7 | 0.13 | 1.01 |
| | | 10 | 15 | 0.03 | 0.27 |
| | | 50 | 50 | 0.07 | 0.57 |
| | | 100 | 100 | 0.07 | 0.57 |
| | 3 | 145 | 68 | 0.23 | 1.81 |
| | 2 | 300 | 45 | 0.95 | 7.13 |
| | | 400 | 100 | 0.52 | 4.03 |
| | | 600 | 100 | 0.84 | 6.37 |
| | | 800 | 100 | 1.17 | 8.62 |
| | | 1000 | 100 | 1.49 | 10.78 |
| | | 1500 | 100 | 2.29 | 15.77 |
| Thin outer shell | | 10 | 2 | 0.68 | 5.21 |
| | 4 | 37 | 6 | 0.87 | 6.56 |
| | | 50 | 2 | 3.85 | 24.26 |
| | | 100 | 2 | 7.55 | 39.52 |
| | | 200 | 2 | 14.16 | 56.90 |
| | 1 | 365 | 20 | 2.80 | 18.73 |
| | | 600 | 10 | 8.95 | 44.03 |
| | | 800 | 10 | 11.64 | 51.30 |
| | | 1000 | 10 | 14.16 | 56.90 |
| | | 1500 | 10 | 19.89 | 66.52 |

Typically, the microcapsules of the invention have a mean core radius size of between 5 μm and 1,000 μμm. Microcapsules having a mean core radius size between 100 μm and 500 μm have proved useful in certain body care products. In other cases, microcapsules wherein the mean core radius size was between 10 and 40 μm also proved to be useful. The size of the microcapsules can be easily adjusted by the skilled person as a function of the nature of the desired application The volume of the inner shell typically represents 0.1 to 80% of the total volume of the shell.

The final composite membrane properties depend on multiple factors such as the monomer concentration within the capsule core. The initial thickness of the capsule membrane also affects the final composite membrane properties. The concentration of the monomer is adjusted to ensure that the concentration of the free monomer in the final product is below safety requirement.

The perfume oil in the internal phase of the microcapsules of the invention may comprise a single compound or a mixture of compounds. Non-limiting examples of active perfuming ingredients susceptible of being advantageously encapsulated according to the invention are as follows:

2,6,10-Trimethyl-9-undecenal
2-Propenyl hexanoate
cis-3-Hexenyl 2-methylbutanoate
Decanal
cis-3 -Hexenyl-methyl-carbonate
Nonanal
9-Decen-1-ol
Methyl-3-heptanone oxime
(2S,5R)-2-Isopropyl-5-methylcyclohexanone
1,7,7-Trimethylbicyclo[2.2.1]heptan-2-one
para tert-Butylcyclohexanone
Isobornyl acetate
Cyclohexyl 2-hydroxybenzoate
Allyl cyclohexyl propionate
Dihydroterpenyl acetate
2,4,6-Trimethyl-4-phenyl-meta-dioxane
2-Heptyl-1-cyclopentanone
(3,4-Dihydroxyphenyl)acetate
Trimethyl cyclodecatrine epoxide
6 Ethyl-3,10,10-trimethyl-4-oxaspiro[4.5]deca-1,6-diene
4-tert-Butyl-cyclohexyl acetate
1-(1-Ethoxyethoxy)propane
Allyl (2-methylbutoxy)acetate
Prop-2-enyl2-(3-methylbutoxy)acetate
1-Octen-3-ol
trans-Anethole
3-(4-tert-Butylphenyl)propanal
2,6-Nonadien-1-ol
[(3,7-Dimethyl-6-octenyl)oxy]-acetaldehyde
Lauronitrile
2,4-Dimethyl-3-cyclohexene-1-carbaldehyde
1-(2,6,6-Trimethyl-1,3-cyclohexadien-1-yl)-2-buten-1-one
1-(2,6,6-Trimethyl-2-cydohexen-1-yl)-, (E)-2-buten-1-one
gamma-Decalactone
trans-4-Decenal
2-Pentyl cyclopentanone
1-(2,6,6 Trimethyl-3 -Cyclohexen-1-yl)-2-Buten-1-one)
1,1'-oxybis-Benzene
1-(5,5-Dimethyl-1-cyclohexen-1-yl-4-enten-1-one
Ethyl-2-methylbutanoate
1,3,3-Trimethyl-2-oxabicyclo[2.2.2]octane
Eugenol
3-(3-Isopropylphenyl)butanal
Methyl2-octynoate
4-(2,6,6-Trimethyl-1-cyclohexen-1-yl-3 -buten-2-one
2-Methoxy-3-(2-methylpropyl)-pyrazine
Isobutyl quinoline
Isoeugenol
Tetrahydro-6-(3-pentenyl)-2H-Pyran-2-one The microcapsules of the present invention have multiple uses. For example, the microcapsules of the invention can be included in perfumery applications where capsules made by coacervation or by interfacial polymerization can be used, including but not limited to, consumer products such as, body wash, body care, air care and fine fragrances. In one embodiment, capsules with strong adhesive properties, are preferred. Whereas strong adhesive properties have been described for certain polyelectrolyte complexes found in nature, it has until now been impossible to achieve coacervate-based adhesion mechanisms for microcapsules while also retaining the outstanding, low permeability, barrier properties provided by synthetic polyurea shells. Surprisingly, the presence of the coacervate component of the shell formed by the protein and the weakly anionic polyelectrolyte provides outstanding adhesive properties to the capsules of this invention.

The microcapsules of the invention described herein can be used as perfuming ingredients in consumer products of the home- or personal-care type. This result is highly surprising since the consumer products contain high amounts (typically more than 10% of their own weight) of specific type of surfactant/tensioactive/solvents which are known to significantly diminish the stability and the performance of other similar prior art capsules. The use of the microcapsules disclosed herein provides improved deposition of the perfume on the treated surface together with an improved stability in a chemically aggressive environment. In other words, the use of the capsules in various applications provides unforeseeable advantages over the same use of other similar prior art capsules.

The present invention also relates to the use of such microcapsules in a consumer product that is in the form of a home- or personal-care product. Such products may be either a solid or a liquid product. According to a particular embodiment, liquid products are preferred. The expression "home- or personal-care" has here the usual meaning in the art, and in particular, it includes products such as body-care, hair-care or home-care products. Examples of liquid products according to the invention may be selected from the group consisting of a shampoo or a hair conditioner, a liquid detergent, a fabric softener, a shower or bath mousse, oil or gel, a deodorant or an antiperspirant. Preferably, the liquid perfumed product is a shower gel, shampoo, a liquid detergent or a fabric softener. Examples of solid products according to the invention may be selected from the group consisting of a soap bar, a powder detergent or an air-freshener. As detergent products, there are considered applications such as detergent compositions or cleaning products for washing up or for cleaning various surfaces, for example, intended for textiles, dishes or hard surfaces (floors, tiles, stone-floors, etc). Preferably, the surface is a textile.

Conveniently, the microcapsules of the invention may be used as such to perfume the consumer products. For example, the microcapsules may be directly added to a consumer product in an amount of 0.1-30 wt. %, e.g. resulting in a total perfume content of about 0.0333-10 wt. %. Preferably, a consumer product according to the invention comprises about 0.01 to 4 wt. %, or even 4.5%, of its own weight, in capsules as defined above and containing the perfume oil ingredients. Of course, the above concentration may be adapted according to the olfactive effect desired in each product.

The invention also provides consumer products such as a laundry and cleaning composition comprising microcapsules of the invention and a detersive ingredient. Preferably, the laundry and cleaning composition is selected from the group consisting of a detergent composition, a hard surface cleaning composition, and a dishwashing composition. The invention also provides a process for making such laundry and cleaning composition, which comprises the step of combining the microcapsules of the invention, by means selected from spraying, dry-mixing, and mixtures thereof, with the detersive ingredient.

Most preferably, the laundry and cleaning composition is a fabric detergent or softener composition. Typical examples of fabric detergent or softener composition into which the microcapsules of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Another advantage of the invention is that the microcapsules as disclosed herein results in beneficial effects on the retention of the perfume oil ingredients in the microcapsules over time. Thus, the aging process of the microcapsules is reduced, such that the microcapsules or products containing them can be stored over time for longer periods compared to other formulations of microcapsules that are not prepared as noted herein. Thus, the present invention increases the shelf life of home- or personal-care products that contains these microcapsules.

Depending on the safety status of the final product, the microcapsule of the invention may also be used in food applications where capsules made by coacervation are commonly used.

EXAMPLES

The following non-limiting examples are illustrative of the present invention.

Example 1

Multilayered Polyurea/Coacervate Capsules Cross-Linked with Glutaraldehyde

Aqueous solutions of (A) 10% wt. pork gelatine (250 Bloom, supplied by Norland); (B) 10% wt. gum arabic (EFFICACIA®, from CNI); and (C) 3% wt. guanazol are prepared separately. The fragrance component to be encapsulated is mixed with (D) 8% of isocyanate (Desmodur® N4; origin: Bayer Material Science).

In a vessel at 40° C., 25.4 g of solution (A) and 12.7 g of solution (B) are added to 92.8 g of warm demineralised water under mechanical shear. The pH is adjusted to 4.5 using HCl 1M. The mixture is maintained at 40° C. for 15 min and then cooled down to 35-31° C. at a rate of 0.5° C. min$^{-1}$.

19.1 g of solution (D) is slowly added to the mixture and homogenised at 350 RPM for a period of 5 min, so as to reach an average droplet size of 300 µm. Mechanical shear is maintained while the solution is let to cool down at 10° C. at a rate of 0.5° C. min$^{-1}$. The stirring speed is then slightly decreased, and 0.102 g of glutaraldehyde (aq.50% wt. Supplied by Sigma-Aldrich) is added to the mixture. Cross-linking is allowed to proceed for 4 to 10 hours at 20° C.

20 g of solution (C) is then added to the aqueous suspension of microcapsules at a rate of 1 ml/min. The mixture is kept under agitation for 1 to 4 hours at room temperature or optionally heated to temperature between 40-70° C.

The result is an aqueous suspension of multilayered capsules with composite polyurea/coacervate shells, the coacervate component being formed by gelatin and gum arabic.

These capsules were inspected visually using microscopy. Rupturing the capsules (for example, by exerting mechanical force onto the capsules with mortar and pestle or by squeezing them between two glass slides) and subsequent observation in the microscope indicates that even upon fracture of the entire capsule, the individual layers of the formed multilayer shells remain interlinked. No delamination of the coacervate from the polyurea is observed, indicating that indeed the multilayer capsule shells formed are a composite, interlinked material.

Example 2

Multilayered Polyurea/Coacervate Capsules Cross-Linked Enzymatically with Transglutaminase Solution (A') is an aqueous solution of 10% wt. Warm water fish gelatine (230 Bloom, supplied by Wheishardt).

In a vessel at 40° C., 25.4 g of solution (A') and 12.7 g of solution (B) (see Example 1) are added to 92.8 g of warm demineralised water under mechanical shear. The pH is adjusted to 4.5 using HCl 1M. The mixture is maintained at 40° C. for 15 min and then cooled down to 35-31° C. at a rate of 0.5° C. min$^{-1}$.

19.1 g of solution (D) (see Example 1) is slowly added to the mixture and homogenised at 350 RPM during 5 min, so as to reach an average droplet size of 300 µm. Mechanical shear is maintained while the solution is let to cool down at 10° C. at a rate of 0.5° C. min$^{-1}$. The stirring speed is slightly decreased, the pH is adjusted to 4.5 and 1.01 g of transglutaminase (ACTIVA® WM supplied by Ajinomoto) is added to the mixture. Cross-linking is allowed to proceed for 4 to 10 hours at 20° C.

20 g of solution (C) (see Example 1) is then added to the aqueous suspension of microcapsules at a rate of 1 ml/min The mixture is kept under agitation for 1 to 4 hours at room temperature or optionally heated to temperature between 40-70° C.

Example 3

Multilayered Polyurea/Coacervate Capsules Prepared by Initial In-Situ Polymerization Within a Coacervate Shell Followed by Cross-Linking In a vessel at 40° C., 25.4 g of solution (A') and 12.7 g of solution (B) (see Example 1) are added to 92.8 g of warm demineralised water under mechanical shear. The pH is adjusted to 4.5 using HCl 1M. The mixture is maintained at 40° C. for 15 min and then cooled down to 35-31° C. at a rate of 0.5° C. min$^{-1}$.

19.1 g of solution (D) (see Example 1) is slowly added to the mixture and homogenised at 350 RPM for 5 min, so as to reach an average droplet size of 300 µm. Mechanical shear is maintained while the solution is let to cool down at 10° C. at a rate of 0.5° C. min$^{-1}$ and maintained at 10° C. for 1 hour. The aqueous suspension of microcapsules is then warmed up to room temperature and 20 g of solution (C) (see Example 1) is then added to the aqueous suspension of microcapsules at a rate of 1 ml/min The mixture is kept under agitation for 1 to 4 hours at room temperature.

Finally, 0.102 g of glutaraldehyde (aq. 50% wt. Supplied by Sigma-Aldrich) is added to the mixture and cross-linking is allowed to proceed for 4 to 10 hours at 20° C.

Example 4

Multilayered Polyurea/Coacervate Capsules (Thin Shell) Cross-Linked with Glutaraldehyde In a vessel at 40° C., 19.1 g of solution (A) (see Example 1) and 19.1 g of solution (B) (see Example 1) are added to 92.8 g of warm demineralised water under mechanical shear. The pH is adjusted to 4.4 using HCl 1M. The mixture is maintained at 40° C. for 15 min and then cooled down to 35-31° C. at a rate of 0.5° C. min$^{-1}$.

19.1 g of solution (D) (see Example 1) is slowly added to the mixture and homogenised at 350 RPM for 5 min, so as to reach an average droplet size of 300 μm. Mechanical shear is maintained while the solution is let to cool down at 10° C. at a rate of 0.5° C. min$^{-1}$. The stirring speed is slightly decreased, and 0.102 g of glutaraldehyde (aq.50% wt. Supplied by Sigma-Aldrich) is added to the mixture. Cross-linking is allowed to proceed for 4 to 10 hours at 20° C.

20 g of solution (C) (see Example 1) is then added to the aqueous suspension of microcapsules at a rate of 1 ml/min The mixture is kept under agitation for 1 to 4 hours at room temperature or optionally heated to temperature between 40-70° C.

Example 5

Multilayered Polyurea/Coacervate Capsules (Corpuscular Shell) Cross-Linked with Glutaraldehyde In a vessel at 40° C., 12.7 g of solution (A) (see Example 1) and 25.4 g of solution (B) (see Example 1) are added to 92.8 g of warm demineralised water under mechanical shear. The pH is adjusted to 4.0 using HCl 1M. The mixture is maintained at 40° C. for 15 min and then cooled down to 35-31° C. at a rate between 1.5 and 0.5° C. min$^{-1}$.

19.1 g of solution (D) (see Example 1) is slowly added to the mixture and homogenised at 350 RPM for 5 min, so as to reach an average droplet size of 300 μm. Mechanical shear is maintained while the solution is let to cool down at 10° C. at a rate of 0.5° C. min$^{-1}$. The stirring speed is slightly decreased, and 0.102 g of glutaraldehyde (aq.50% wt. Supplied by Sigma-Aldrich) is added to the mixture. Cross-linking is allowed to proceed for 4 to 10 hours at 20° C.

20 g of solution (C) (see Example 1) is then added to the aqueous suspension of microcapsules at a rate of 1 ml/min The mixture is kept under agitation for 1 to 4 hours at room temperature or optionally heated to temperature between 40-70° C.

Figure 6:
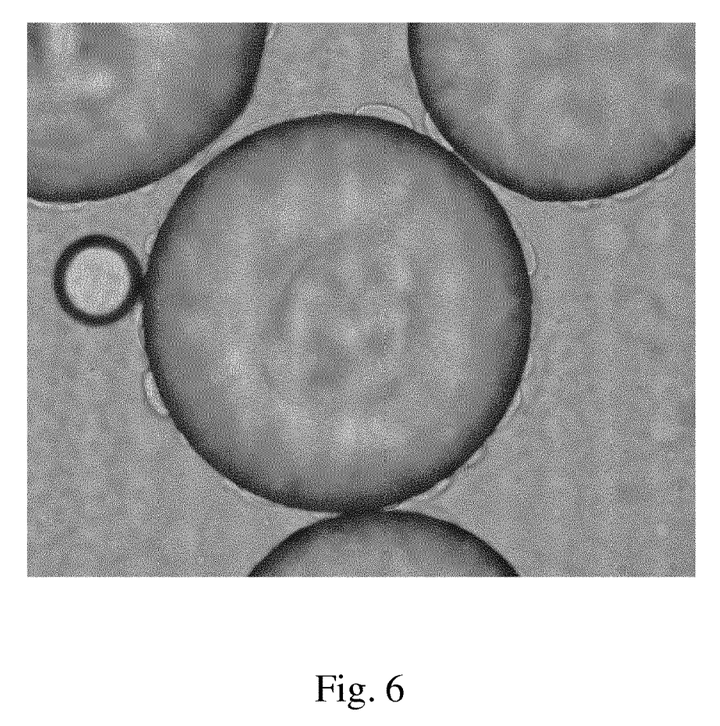
FIG. 6 shows exemplary capsules of the invention having a corpuscular shell.

The resulting capsules exhibit a corpuscular shell as shown FIG. 6

Example 6

Improved Stability in Surfactant Solution

Figure 2:
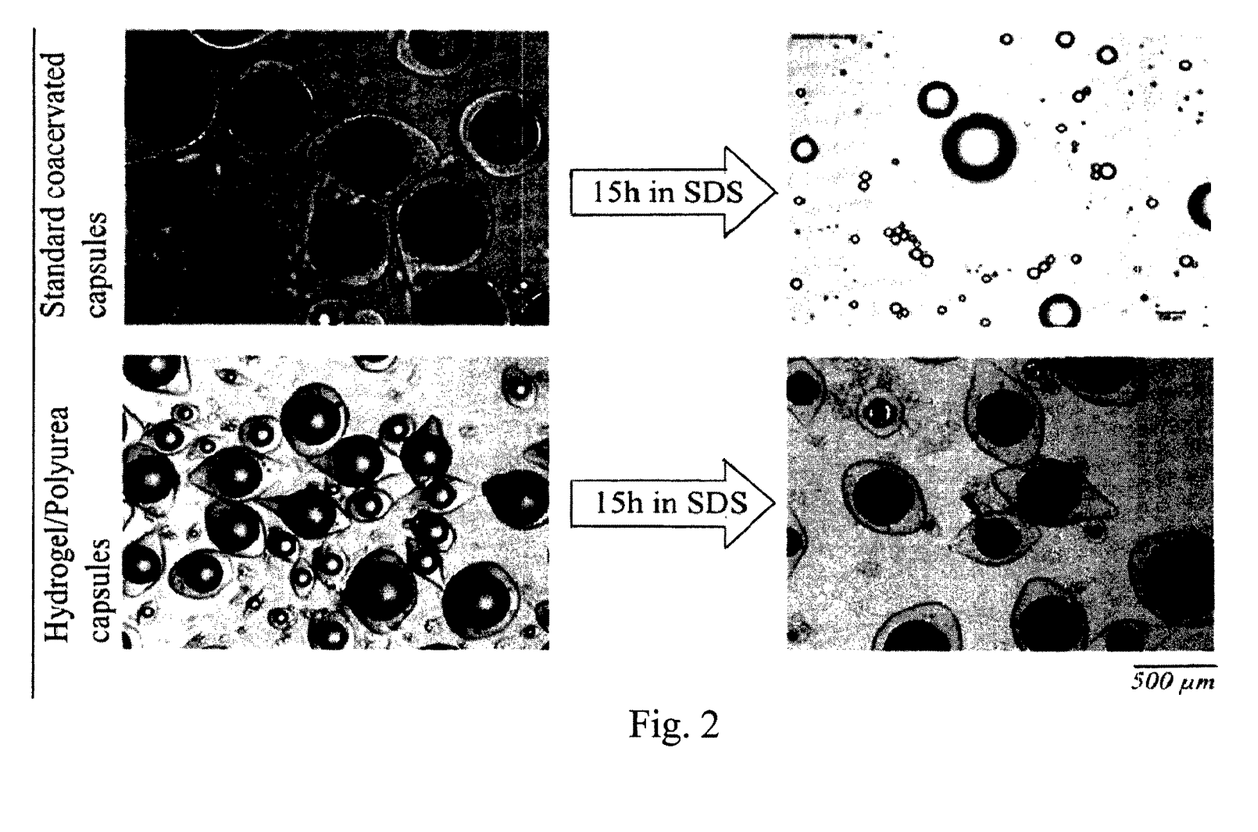
FIG. 2 shows a side-by-side comparison between standard coacervated capsules and the multilayered coacervate/polyurea core/shell capsules in a surfactant solution.

The stability of standard coacervated capsules, prepared in a manner similar to that described by Meyer A., Perfume microencapsulation by complex coacervation, Chimia 46 (1992) 101-102, and hydrogel/polyurea capsules of the invention, were compared. As shown in FIG. 2, the hydrogel/polyurea capsules prepared as described in Example 1 were found to be significantly more stable than the standard coacervated capsules. In particular, after 15 hours in SDS, the shells of the standard coacervated capsules were completely destroyed, thus releasing the encapsulated material. In contrast, the shells of the hydrogel /polyurea capsules of the invention remained intact after 15 hours in SDS, thus preventing the premature release of the encapsulated material. This result shows that the presence of the inner synthetic polymer (polyurea) within the hydrogel shell significantly improves the stability of the capsules, even when applied in aggressive, highly concentrated surfactant media.

Example 7

Improved Stability in a Shower Gel Application

The stability of standard coacervated capsules, prepared in a manner similar to that described by Meyer A., Perfume microencapsulation by complex coacervation, Chimia 46 (1992) 101-102.) and the hydrogel/polyurea capsules of the invention were compared in a shower gel. The model shower gel base used was composed of 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value.

Figure 3:
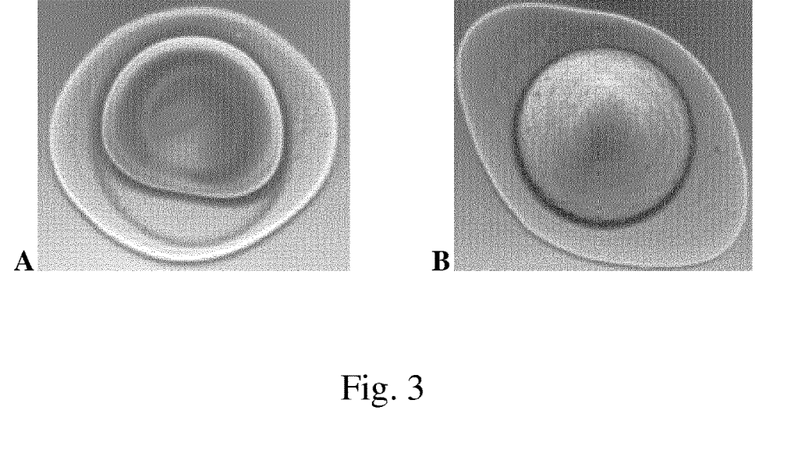

The standard capsules contained the same active agent as in the internal phase of the hydrogel /polyurea capsules. As shown in FIGS. 3A and B, the hydrogel/polyurea capsules prepared as described in Example 1 are significantly more stable than the standard coacervated capsules. In particular, after 24 hours in the shower gel, standard coacervated capsules have a 65% leakage while no leakage is found in the hydrogel/polyurea capsules of the invention, thus preventing the premature release of the encapsulated material. This result further demonstrates that the presence of the inner synthetic polymer (polyurea) within the hydrogel shell significantly improves the stability of the capsules when subjected to highly concentrated surfactant media.

Example 8

Figure 7:
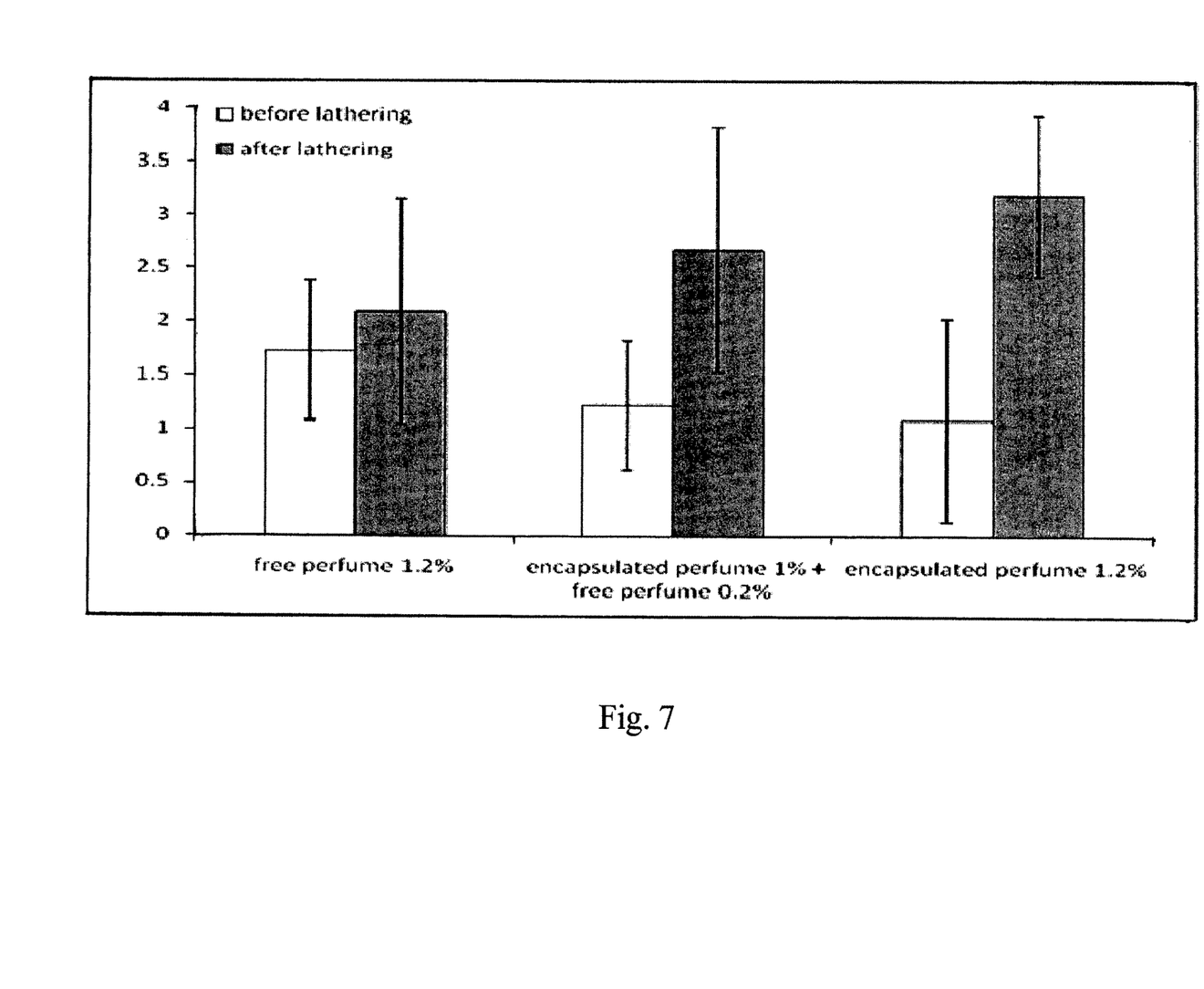
FIG. 7 shows results from an evaluation of capsules of the invention in a shower gel composition, with the perfume intensity rated by an untrained panel

Evaluation of Capsule Performance in a Model Shower Gel Composition: 'Blooming' Effect Upon Lathering Multilayered capsules were prepared as described in Example 1. The release properties of the capsules were evaluated in a model shower gel base (see composition in Example 7) in panel tests with twelve untrained participants. The perfume was a model perfume composition with predominantly citrus and fruity notes. The panelists were asked to rate the perceived perfume intensity of the shower gel before usage (5 ml of shower gel held in the palm of the panelist's hands) and after lathering for ten seconds with warm water. The panelists were asked to rate the 'before' and 'after' samples on a scale of 0 to 4 (0: no perfume perceived, 1: weak; 2: medium; 3: strong; 4: very strong). This test was performed on three different samples, each tested individually but by the same group of panelists. Sample A: shower gel containing 1.2% w/w free perfume; Sample B: shower gel containing 1.2% w/w encapsulated perfume according to example 5; Sample C: shower gel containing 1% w/w encapsulated perfume according to example 5 and 0.2% w/w free perfume. Key results of the panel test are summarized in FIG. 7; shown are the mean values of the panelists' intensity ratings along with the standard deviation. Only a minor increase in perceived intensity upon lathering was observed for the free perfume (Sample A). In contrast, if the perfume was present in encapsulated form, a significant and very strong difference was perceived by all of the panelists, with mean intensity values increasing from 1.1 to 3.1 upon lathering. The effect was still very strong even if a smaller amount of capsules was added in combination with a small amount of free oil.

Example 9

Use of the Perfume Capsules to Provide Sequential Delivery of Two Perfumes in a Model Shower Gel Composition Upon Lathering This example demonstrated the capacity of the capsules to provide sequential delivery properties in a consumer product such as a cosmetic cream or lotion, shower gel, or a liquid soap/handwash. The objective was to first deliver a perfume (perfume 1) added to the base as a liquid (without being encapsulated encapsulation), and to add another perfume (perfume 2) in encapsulated form. Upon application of the product, the panelists should perceive predominantly perfume 1 when smelling the neat shower gel before lathering, but not perfume 2. Then, upon lathering, perfume 2 should be released when the capsules are broken due to mechanical rubbing. Multilayered capsules were prepared as described in Example 1. The release properties of the capsules were evaluated in a model shower gel composition in panel tests with twelve untrained participants. Here, perfume 1 was of a floral note ('muguet' type) and perfume 2 was a composition with predominantly citrus and fruity notes. As in example 8, the panelists were asked to rate the perceived perfume tonality of the shower gel before usage (5 ml of shower gel held in the palm of the panelist's hands) and after lathering for ten seconds with warm water.

The sample to be evaluated is a shower gel base (see composition in example 7) containing 1.0% w/w encapsulated perfume 2 according to example 5 and 0.2% w/w free perfume 1 The panelists were asked to describe the 'before' and 'after' samples by choosing from a provided list of descriptors ("floral", "green", "fresh", "fruity", "citrus", "watery") but were also asked to provide any additional descriptors of their choice. Furthermore, the panelists were asked generally if they perceived a change in tonality upon lathering ("yes", "no" or "not sure" question), and if they perceived a overall increase in intensity upon lathering ("yes", "no" or "not sure" question). The ratings were then collected and summarized. Before lathering, the top counts descriptors were "floral" (by 83% of the panelists), "green" (by 42% of the panelists), or "soap-like" (by 16% of the panelists). After lathering, the top descriptors were "citrus" (by 83% of the panelists), "fruity" (by 54% of the panelists), "fresh" (by 25% of the panelists); additional free descriptors mentioned spontaneously by the panelists were "grapefruit" and "passion fruit". After lathering, 100% of the panelists perceived an overall increase in perfume intensity. 83% of the panelists perceived a clear and unambiguous change on tonality upon lathering, whereas 17% of the panelists were not sure.

Example 10

Characterization of the Mechanical Properties of the Composite, Interlinked Shell Material To characterize the composite, interlinked layer of the shell material, mechanical tests were performed using the method of interfacial rheology. Such experiments allow for precise measurement of the elastic shear modulus of the interfacial film. The theory and details of interfacial rheology measurements are described in detail in the scientific literature (for example: "Interfacial transport processes and rheology" by D. A. Edwards, H. Brenner and D. T. Wasan, Butterworth-Heinemann, Boston Mass., USA, 1991). Interfacial polymerization leads to a strong increase of the elastic shear modulus of the interface, G'i (measured in units of Newtons per meter). In contrast, if no polymerization occurs, the elastic shear modulus of the interface is undetectable. Equipment for interfacial rheology measurements is available from a variety of instrument manufacturers (such as Anton Paar, Germany; TA Instruments, USA; or KSV Instruments, Finland). For characterization of the interfacial films described here, an Anton Paar MCR300 instrument is used, and the measuring setup used is a biconical disk geometry, following the methods described in detail in the literature (P. Erni et al., Review of Scientific Instruments, Vol. 74, pp 4916-4924).

Interfacial rheology measurements were performed for three different situations to elucidate the interlinked nature of the shell material. In all cases, the temperature was 45° C.

1. A control experiment was performed by measuring the elastic shear modulus of the interface between amine-free and polyelectrolyte-free (in particular, gelatin-free) water adjusted to three different pH values (pH 2, pH 7, and pH 11) on one side, and the fragrance oil containing 8% of the oil-soluble isocyanate monomer on the other side. This control experiment was performed to confirm that the isocyanate did not polymerize with any components (for example: nitrogen-containing impurities) in the absence of amines and in the absence of gelatin. The result was that in the absence of amines and in the absence of gelatin in the water phase, the elastic shear modulus of the interface was always zero, G'i=0, indicating that indeed no polymerization occurs.

2. A second control experiment was performed to measure the elastic shear modulus of the interface G'i for single layer, polymer-only shell materials. In this experiment, the water phase was an aqueous amine solution (3% guanazol in deionized water) at pH 11 and the oil phase was again the fragrance component containing 8% isocyanate. As expected, significant polymerization occurred and values for G'i could already be detected after two minutes of polymerization. The interfacial modulus increased over the course of an hour and attained a value of 0.7 N/m after 190 minutes, and then remained constant.

3. A third control experiment was performed to verify that the polyelectrolyte (gelatin) alone did not form an elastic interfacial film at the temperature studied (45° C., which is above the melting temperature of the gelatin). A solution of gelatin (type A, 275 Bloom) at 0.5% at pH 4.5 was prepared, and brought into contact with the monomer-free fragrance oil. The elastic shear modulus of the interface remained at zero during 36 hours, G'i=0, indicating that gelatin does not form an elastic firm at this temperature. Furthermore, it was also verified seperately that the gelatin did form a bulk gel but remained in solution at this temperature.

4. The main experiment was performed to assess whether or not the polyelectrolyte (gelatin) participates in the interfacial polymerization. A solution of gelatin (type A, 275 Bloom) at 0.5% at pH 4.5 was prepared, brought into contact with the fragrance oil containing 8% isocyanate, and the elastic shear modulus of the interface G'i was measured. No amines were added to the water phase, therefore the presence of 0.5% gelatin was the only difference to the control experiment No. 1 described above in this example. Surprisingly, after 30 minutes, increasingly strong values of the elastic shear modulus of the gelatin/isocyanate interface could be detected, and G'i steadily increased during the course of the experiment. After 10 hours at a temperature of 45° C., the modulus had increased to a value of 0.01 N/m. Additional addition of free amines (3% guanazol) in the aqueous solution and change of the pH to 11 further increases G'i. This experiment demonstrates that gelatin is intimately integrated into the composite, interlinked shell layer and that interfacial polymerization already occurs between the gelatin and the isocyanate, before additional free amines are added.

What is claimed is:

1. A method of making interlinked multilayer microcapsules, which comprises:

providing as a dispersion in an aqueous vehicle, a hydrophobic internal phase comprising a monomer and an active agent of a fragrancing or flavoring component;

providing a complex coacervation by mixing a first and second polyelectrolytes in the aqueous vehicle under conditions sufficient to form a suspension of complex coacervate nodules;

first depositing the complex coacervate nodules at an interface of an aqueous vehicle adjacent the hydrophobic internal phase to initially form an outer shell of the microcapsule, wherein the hydrophobic internal phase forms the core and contains the monomer and a fragrancing or flavoring component therein; and subsequently introducing a water soluble reactant into the aqueous vehicle under conditions sufficient to induce interfacial polymerization of the monomer inside the outer shell to thereafter form an inner shell at the interface between the internal phase and the outer shell.

2. The method of claim 1, wherein the first polyelectrolyte carries a net positive charge when the pH is less than 8 while the second polyelectrolyte carries a net negative charge when the pH is greater than 2.

3. The method of claim 2, wherein the first polyelectrolyte is gelatin and the second polyelectrolyte is selected from the group consisting of carboxymethyl cellulose, sodium carboxymethyl guar gum, xanthan gum and plant gums.

4. The method of claim 3, wherein the second polyelectrolyte is acacia gum.

5. The method of claim 1 which further comprises cross-linking the core-shell capsule chemically or enzymatically before introducing the reactant into the aqueous vehicle.

6. The method of claim 1, wherein the pH and the temperature of the aqueous vehicle are adjusted before during or after the introduction of reactant to control the rate of interfacial polymerization.

7. The method of claim 1, wherein the microcapsule's inner shell has a volume that is between 0.1 and 80% of the volume of the outer shell.

8. The method of claim 1, wherein the fragrancing or flavoring component is a perfume or flavor oil.

9. The method of claim 1, wherein the inner and outer shells are present as interlinked layers.

10. The method of claim 9, wherein the multilayer microcapsules that are produced include the coacervate as the outer shell, the polymer as the inner shell, and the active agent in the internal phase.

11. The method of claim 10, wherein the fragrancing or flavoring component is a perfume or flavor oil.

12. The method of claim 1, wherein the multilayered microcapsules that are produced are added to a consumer product in the form of a home- or personal-care product in liquid or powder form.

13. The method of claim 12, wherein the consumer product is a detergent composition, a fabric softener, a hard surface cleaning composition, a dishwashing composition, a shampoo, a hair conditioner, a shower or bath mousse, oil or gel, a deodorant, or an antiperspirant.

14. A method of making interlinked multilayer microcapsules, which comprises:

providing as a dispersion in an aqueous vehicle, a hydrophobic internal phase comprising a monomer and an active agent of a fragrancing or flavoring component;

mixing a first and second polyelectrolytes in the aqueous vehicle under conditions sufficient to form a suspension of complex coacervate nodules;

depositing the complex coacervate nodules at an interface of an aqueous vehicle adjacent the hydrophobic internal phase to form an outer shell of the microcapsule, wherein the hydrophobic internal phase forms the core and contains the monomer and fragrancing or flavoring component therein; and introducing a water soluble reactant into the aqueous vehicle under conditions sufficient to induce interfacial polymerization of the monomer inside the outer shell to form an inner shell at the interface between the internal phase and the outer shell, wherein the monomer is an oil soluble isocyanate, and the reactant is guanazole, guanidine, or a salt thereof.

* * * * *